United States Patent [19]

Wascher et al.

[11] Patent Number: 4,961,747
[45] Date of Patent: Oct. 9, 1990

[54] IMPLANTABLE ARTICIFICAL BLADDER SYSTEM

[75] Inventors: Uwe Wascher, Lenox, Mass.; Jacek L. Mostwin, Baltimore, Md.; Lorne Belden, Jr.; Gerald Kushner, both of Louisville, Ky.

[73] Assignee: General Electric Company, Pittsfield, Mass.

[21] Appl. No.: 279,600

[22] Filed: Dec. 5, 1988

[51] Int. Cl.⁵ .............................................. A61F 2/04
[52] U.S. Cl. .......................................... 623/12; 623/3
[58] Field of Search ...................................... 623/12, 3

[56] References Cited

U.S. PATENT DOCUMENTS

| | | | |
|---|---|---|---|
| 3,953,897 | 5/1976 | Chevallet et al. | 623/12 |
| 4,044,401 | 8/1977 | Guiset | 623/12 |
| 4,228,550 | 10/1980 | Salkind | 623/12 |
| 4,623,350 | 11/1986 | Lapeyre et al. | 623/3 |
| 4,820,300 | 4/1989 | Pierce et al. | 623/3 |

FOREIGN PATENT DOCUMENTS

| | | |
|---|---|---|
| 2655034 | 6/1978 | Fed. Rep. of Germany . |
| 2116838 | 7/1972 | France ........................... 623/12 |

Primary Examiner—Randall L. Green
Assistant Examiner—Stephanie L. Iantorno
Attorney, Agent, or Firm—Hedman, Gibson, Costigan & Hoare

[57] ABSTRACT

Implantable artificial bladder and method for the collection of, the storage of, or the discharge of biological fluids using the natural peristaltic pressure of a patient's ureter or ureters or of an artifical ureter to fill a first chamber of the artificial bladder and a constant force stored energy means in a second chamber isolated by a rolling diaphragm from the first, said means biasing the rolling diaphragm against the first chamber and serving to empty the implantable artificial bladder.

19 Claims, 5 Drawing Sheets

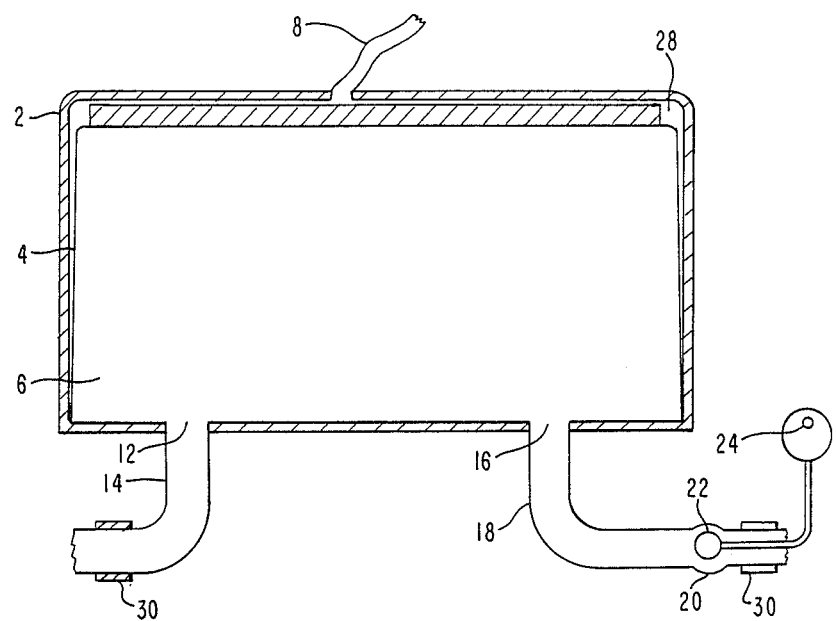
F I G. 2

IMPLANTABLE ARTIFICIAL BLADDER SYSTEM

This invention relates to an implantable artificial bladder for the collection of, the storage of, or the discharge of biological fluids, more specifically urine, in a patient whose natural bladder has failed or has been removed.

BACKGROUND OF THE INVENTION

Loss of the urinary bladder, most commonly due to total cystectomy for muscle invasive carcinoma of the bladder, bladder dysfunction or bladder injury resulting in contraction, stiffness, spasticity or failure to store or to empty urine in a suitable manner are presently being treated with replacement or augmentation of the urinary bladder with intestinal tissue. These operations all have in common either the creation of an intestinal urinary conduit which drains urine continuously into a plastic bag on the patient's abdominal wall or the creation of an internal pouch constructed of intestinal tissue which stores urine inside the patient's abdominal cavity, urine being released either by catheter or newly learned techniques of urination which rely on coordinated abdominal muscle contraction and pelvic muscel relaxation.

Although the simplest of these forms of urinary diversion, the Bricker intestinal conduit or "ileal loop", is a standard and commonly performed surgical procedure, it is the least desirable. A bag must be worn on the abdominal wall which leads to social withdrawal and undesirable change in body image and has been shown to lead to long term damage of the kidneys from infection, obstruction and urinary stone formation.

There has been great interest and activity, as an alternative to this kind of diversion, in the construction of internal urinary reservoirs made of long segments of intestinal tissue. These operations are difficult to perform and usually can be done only in specialized medical centers. There is a considerable increase in risk to the patient. Normal urination will only be possible in a very small select group of men in whom the pouch can be sewn to the natural urinary outlet. In the remaining group of patients, which includes all women, the reservoir must be emptied by intermittent self catheterization introduced by way of an opening in the abdominal wall or the perineum. In addition to the potential for operative complications, the long term effects of redirecting a long segment of intestine from the intestinal tract to a reservoir which provides continuous contact with urine has yet to be determined. Disorders of digestive motility and absorption are common, absorption of urinary waste products through the intestinal wall is common, and the potential for development of cancer in the bowel segment in continuous contact with urine has been recognized, although the extent to which this may become a problem is yet unknown.

Although the use of extensive intestinal substitution and augmentation of the urinary bladder has become popular and safe in the hands of very specialized urological surgeons in a few national medical centers, the long term safety and efficacy remains to be determined, and there is every reason to believe that unexpected difficulties may arise within the next ten years following such reconstruction. There is thus a great need for a totally artificial urinary bladder which would allow patients to undergo complete replacement of the bladder without removal of any segment of the digestive tract.

Sowinski, French Patent No. 2,116,838, discloses an artifical bladder for implantation into the bladder's natural position and for connection to the two ureters and to the urethra of a patient. This bladder comprises a hollow elastic ball which can be elastically deformed to an inflated or to a deflated position under the presence of an auxiliary fluid, surrounding a deformable reception chamber for urine; a system of three internal valves, one of which operates in a direction opposite that of the other two; and a device to control the valves thereby controlling the auxiliary fluid. This bladder is complicated and relatively unreliable.

Chevallet, U.S. Pat. No. 3,953,897, discloses an implantable artificial bladder comprising a flexible plastic pouch which relies upon the internal tensions of the pouch wall in combination with external forces, including the force of the patient's abdominal muscles, to empty the pouch completely and rapidly. Chevallet relied upon the peristaltic effect of the ureter to prevent urine from flowing backwards. However, the combination of the internal tension of the artificial bladder wall and the external pressure of the patient's abdominal muscles could likely be greater than the peristaltic pressure of the ureter, particularly upon the discharging of the contents-of the bladder and therefore could cause urine to flow backwards through the ureters toward the kidneys.

Freier, DE No. 2,655,034, discloses an artificial bladder comprised of stiff plastics and valves to prevent the return flow of urine through the ureters and toward the kidneys.

It is the object of the present invention to provide an implantable artificial bladder and a method for the collection of, the storage of, or the discharge of biological fluids that will allow the patient to function in a nearly normal manner after the removal or the dysfunction of the natural bladder.

A primary advantage of the present invention is that the only pressure needed to empty the bladder is the pressure of a constant force stored energy means which is entirely contained within the implantable artificial bladder. The stored energy derives from the natural peristaltic pressure of the patient's ureter or ureters or from the normal pressure of an artificial ureter, which is utilized to fill the implantable artificial bladder. It is not necessary for the patient to apply any external pressure to fill or to empty the implantable artificial bladder. Indeed, he can not, due to the implantable artificial bladder's rigid shell. Another advantage of the present invention is that it does not have the severe energy demands of a pumped system. A further advantage is that the pressure exerted by the energy stored and used by this invention to empty the implantable artificial bladder does not exceed the normal back pressure or peristaltic pressure of the patient's ureter, and therefore, there will be no resultant backflow of urine through the ureter to the kidneys which would result in damage to those body parts.

BRIEF DESCRIPTION OF THE DRAWINGS

FIG. 2 is an elevation view of an implantable artifical bladder in accordance with this invention with the rolling diaphragm in the full storage volume position.

SUMMARY OF THE INVENTION

According to the present invention, an implantable artificial bladder for the collection of, the storage of, or the discharge of biological fluids is contemplated, the implantable artificial bladder comprising a leak-proof rigid outer shell forming an outer chamber comprised of a material compatible with the organisms surrounding a natural bladder or a material having a surface coating of a material compatible with organisms surrounding a natural bladder; a rolling diaphragm inside the outer chamber and forming a leak-proof inner chamber between the outer shell and the rolling diaphragm, deformable during the introduction and the discharge of the biological fluid between two positions, one corresponding to the full storage volume of the implantable artificial bladder and the other corresponding to the empty volume of the implantable artifical bladder; an external vent in communication with the interior of the outer chamber; a constant force stored energy means operating on said rolling diaphragm and biasing it against said inner chamber; at least one inlet conduit in open communication with the inner chamber and adapted to connect to at least one ureter of a patient, or to an artificial ureter or to a Y-shaped nozzle adapted to connect to both ureters of a patient; at least one outlet conduit in open communication with the inner chamber and below the rolling diaphragm and adapted to connect to the urethra of a patient or to an artifical urethra; and means downstream of the inner chamber of controlling the rate of flow of biological fluid exiting the inner chamber.

The invention in a second major aspect contemplates a method for the collection of, the storage of, or the discharge of biological fluids, e.g., urine, comprising the steps of attaching the inlet conduit of the implantable artificial bladder described above to a patient's ureter, to an artificial ureter attached to at least a portion of a patient's ureter, or to a Y-shaped nozzle attached to a ureter at each of the remaining openings on the Y-shaped nozzle; attaching the outlet conduit of the implantable artificial bladder to the patient's urethra or to an artificial urethra; filling the implantable artificial bladder with biological fluid by the natural peristaltic pressure of the ureter or ureters attached to the inlet conduit or the Y-shaped nozzle; storing the biogicial fluid by closing the means for controlling the rate of flow while storing a portion of the peristaltic pressure as potential energy in the constant force stored energy means; and discharging the biological fluid from within the implantable artificial bladder through the outlet conduit and through the patent's urethra or through an artificial urethra by releasing at least a portion of the energy stored in the constant force stored energy means by opening the means for controlling the rate of flow.

DETAILED DESCRIPTION OF THE INVENTION

Figure 1:
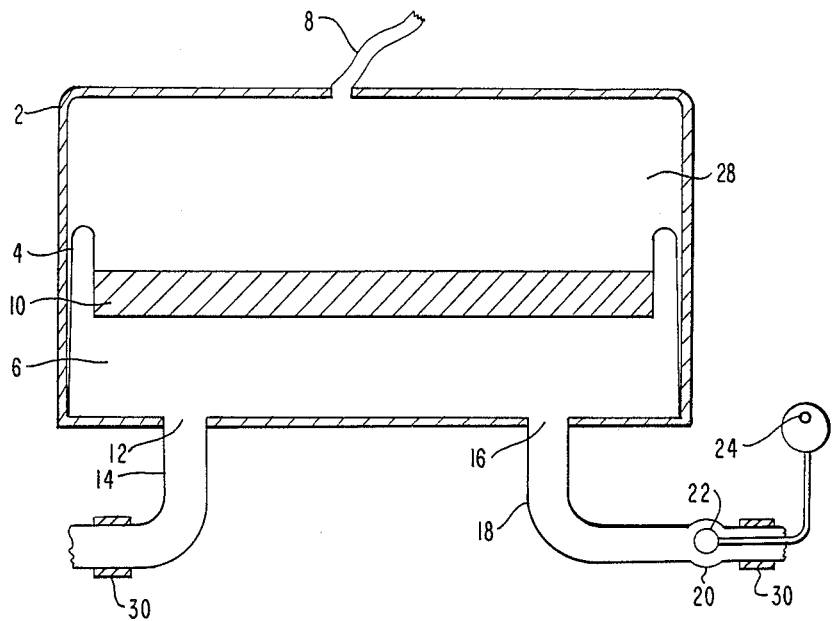
FIG. 1 is an elevation view of an implantable artificial bladder in accordance with this invention.
Figure 3:
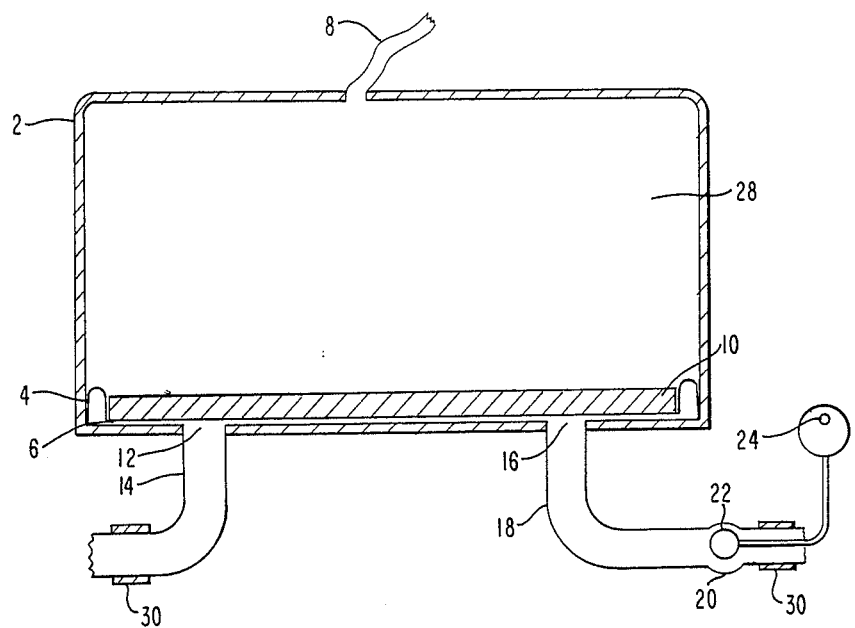
FIG. 3 is an elevation view of an implantable artifical bladder in accordance with this invention with the rolling diaphragm in the empty volume position.
Figure 4:
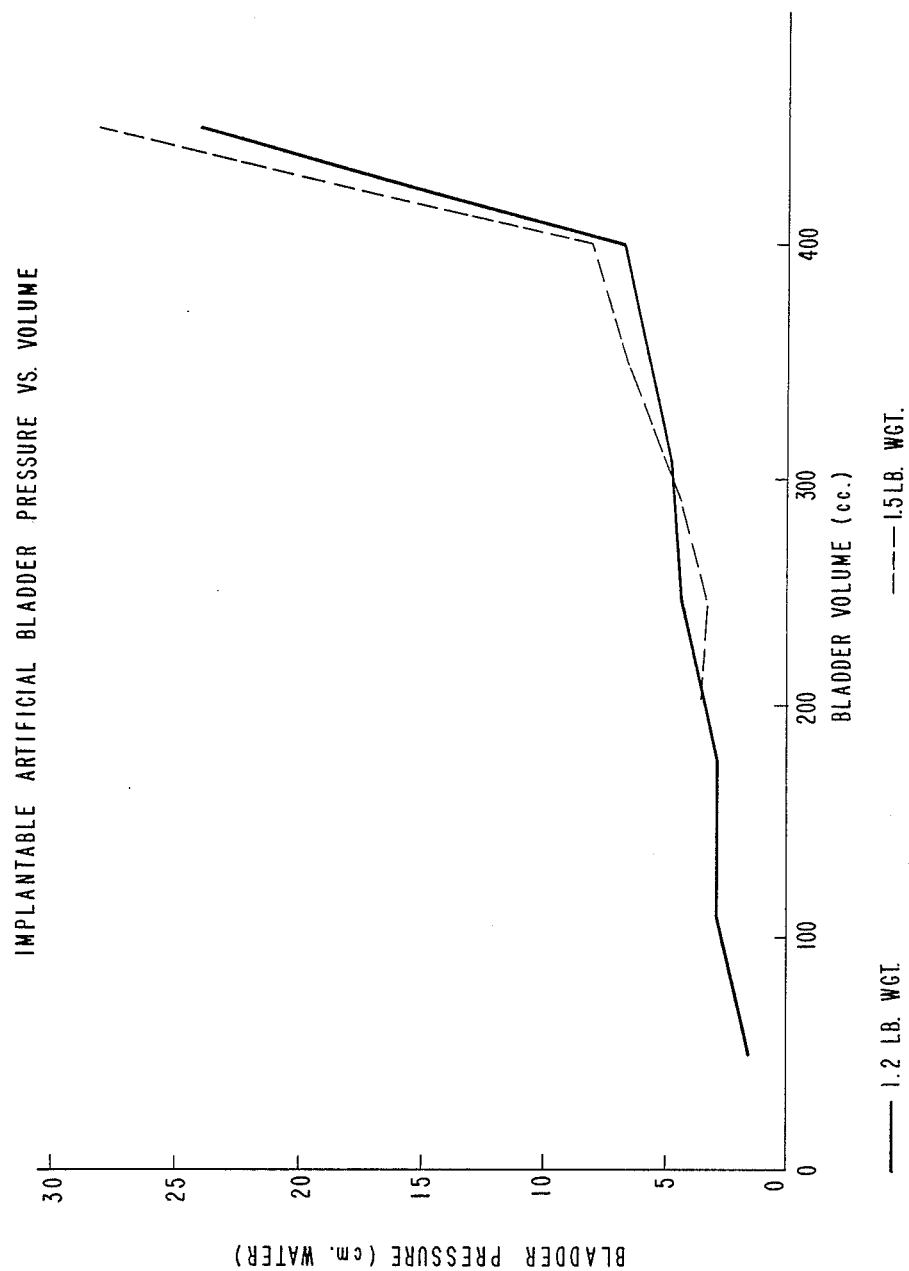
FIG. 4 is a graphic illustration of the relationship between implantable artificial bladder pressure and volume for the preferred embodiments of the present invention.

FIG. 1 illustrates, in schematic form, a cross-section through an implantable artificial bladder for the collection of, the storage of, or the discharge of biological fluids. The biological fluid is preferably urine. A leak-proof rigid outer shell forming an outer chamber 28 which is comprised of material compatible with the organisms surrounding a natural bladder or a material having a surface coating of a material compatible with organisms surrounding a natural bladder encompasses a rolling diaphragm 4, forming a leak-proof inner chamber 6 deformable during the introduction of and the discharge of biological fluids between two positions, that of FIG. 2, a schematic cross-section of the implantable artificial bladder in the full storage position, and that of FIG. 3, a schematic cross-section of the implantable artificial bladder in the empty position. The rigid outer shell 2 can be comprised of a poly(vinyl chloride), a poly(etherimide) or a polymer of acrylonitrile/-butadiene/styrene optionally coated with a material compatible with organisms surrounding a natural bladder including but not limited to silicone or the like. The rolling diaphragm 4 can be comprised of a silicone elastomer, a collagen, a polyactide, a polysuccinate, a polyoxalate, a fluorosilicone, an unsupported silicone or the like. The stiffness of the material of the rolling diaphragm 4 can be varied to change the discharge flow rate of the implantable artificial bladder. The discharge flow rate will be increased if the rolling diaphragm stiffness is reduced and will be decreased if the rolling diaphrgam stiffness is increased. The maximum storage volume of the inner chamber 6 is about 500 ml, small enough to be easily implantable, yet large enough not to require constant or frequent discharge. The relationship of bladder pressure to bladder volume is illustrated in FIG. 4. FIG. 4 graphically demonstrates that the volume selected will be relative to the weight or tension of the stored energy means so that bladder pressure will never exceed the natural peristaltic pressure of the patient's ureter or ureters. However, the volume of the artificial bladder can be increased or decreased by simply enlarging the size of the diaphragm accordingly.

An external vent 8 communicates from the interior of the outer chamber 28 to the area outside the rigid outer shell 2. This vent permits the displacement of the air between the outside of rolling diaphragm 4 and the outer chamber 28 during the deformation and unrolling of the rolling diaphragm 4 during the collection of biological fluid and permits the introduction of air into outer chamber 28 as the rolling diaphragm 4 rolls up and creates a partial vacuum in outer chamber 28 upon the discharge of biological fluid. The diameter of the vent can be either fixed or adjustable so that it can be varied to increase or to decrease the rate at which air can escape the outer chamber 28. The vent 8 can be used to create a dampening effect on movement of the rolling diaphragm 4 and of the constant force stored energy device 10 due to sudden movements or shifts in position by the patient. Most preferably, this vent 8 empties externally to the patient's body. Any possibility of contamination to the patient due the introduction of foreign substances through the vent can be overcome by the placement of a sterile but air-permeable dressing such as gauze over the opening and is inherently overcome by the fact that the vent leads to a space that is completely sealed from and inaccessible to the patient's natural system.

Figure 5:
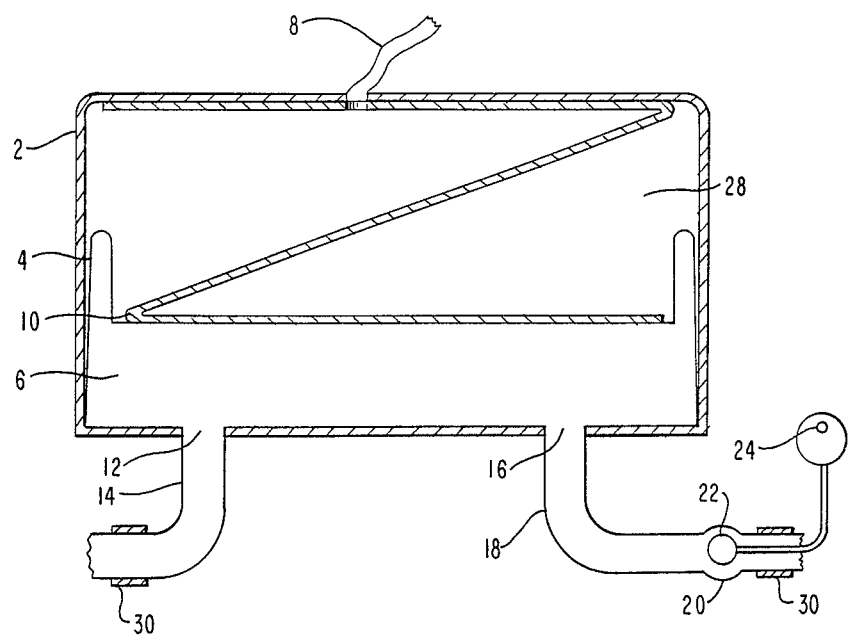
FIG. 5 is an elevation view of an implantable artificial bladder in accordance with this invention.

A constant force stored energy means 10 preferably comprises (a) a weight on the rolling diaphragm located within the outer chamber operating to gravitationally bias the rolling diaphragm into the inner chamber, (b) at least one spring operating against the rolling diaphragm 4 and the interior of the outer chamber 28 as illustrated in FIG. 5 or (c) a combination of (a) and (b). This converts the kinetic energy from the peristaltic pressure of the patient's ureter, which is used to fill the inner chamber with the biological fluid and to deform the rolling diaphragm thereby either raising the weight or compressing the spring, to potential energy which is stored in either the weight as it is raised or the spring as it is compressed by the deformation of the rolling diaphragm to the full volume position. The maximum fill pressure of the leak-proof inner chamber with the constant force stored energy means operating against the rolling diaphragm corresponds to a hydrostatic head of about 15 cm of water which allows the use of the natural peristaltic pressure of the ureter or ureters for the collection of the biological fluid. The maximum static storage pressure of the leak-proof inner chamber with the constant force stored energy means operating against the rolling diaphragm corresponds to a hydrostatic head of about 8 cm of water which prevents damage to the patient's ureter due to backflow. The weight in such a constant force stored energy system should be from about 1.2 lbs to about 1.5 lbs in order to achieve a back pressure through the patient's ureter and kidneys no greater than that naturally found in the patient and no greater than the natural ureter's peristaltic pressure. This eliminates any damage to the patient's ureter or to the patient's kidneys due to back pressure in the static state or during discharge, and permits the patient's natural ureter's peristaltic pressure to be used to fill the implantable artificial bladder. An alignment linkage system can be attached to the constant force stored energy means to eliminate any tilting of the means due to changes in position of the patient such as that between a standing and a reclining position.

There is at least one inlet conduit 14 and one inlet orifice 12 in open communication with the inner enclosure 6 below the rolling diaphragm 4 and adapted to connect to at least one ureter of a patient, to an artificial ureter, or to a Y-shaped nozzle. The Y-shaped nozzle is used when it is necessary to connect two of the patient's ureters to the artificial implantable bladder. Each of the branches of the Y not directly attached to the inlet conduit will be connected to one of the patient's ureters or to an artificial ureter. This nozzle eliminates the need for more than one inlet orifice on more than one inlet conduit. An alternative to the Y-shaped nozzle, should it be necessary to connect more than one ureter to the artificial bladder, would be more than one inlet orifice and inlet conduit, the number of which corresponds to the number of ureters to be connected. The diameter of the inlet conduit and inlet orifice is preferably about 5 mm but could be varied to accommodate different peristaltic pressures supplied by patients suffering from injuries to the ureter.

Additionally, there should be at least one outlet orifice 16 and outlet conduit 18 in open communication with the inner chamber 6 below the rolling diaphragm 4 and adapted to connect to the patient's urethra or to an artifical urethra. It is preferred that this outlet conduit and outlet orifice be about 5 mm in diameter, but the diameter could be varied to increase or to decrease discharge resistance and thereby increase or decrease discharge flow rate and discharge time. The preferred discharge time of an implantable artificial bladder filled with biological fluid is about one minute.

At least a portion of the inlet conduit and of the outlet conduit is preferably encircled with with a collar comprised of suturable and colonizable material 30 such as short-nap velour preferably comprising polyester or polyamide, or woven fabrics comprising polyester to facilitate the attachment of the natural or the artificial ureters and the natural or the artificial urethra. Strips of similar material preferably are attached to surfaces of the rigid outer shell in areas that would likely contact the patient's body so that the implantable artificial bladder can be permanently attached to the patient's body.

A means 20 downstream of the inner chamber 6 controls the discharge of the biological fluid. The means can be placed in either the outlet orifice, in the outlet conduit, in the patient's urethra or in an artificial urethra. The preferred means is a valve of the internal balloon type 22 controlled by an external pump and discharge valve assembly. The internal balloon 22 is inflated with a pump to prevent discharge by obstructing the discharge channel comprised of the outlet orifice, the outlet conduit, the patient's urethra, an artificial urethra, or any combination of the above and is deflated to permit discharge by opening the discharge channel. The means for controlling the flow of the biological fluid is preferably readily removable for cleaning, replacement or repair and comprises a switch 24 to control the pump which is used to operate the internal balloon valve assembly. When the discharge control means is closed, biological fluid can not flow past and any biological fluid passed into the inner chamber 6 will be collected and stored. The peristaltic pressure utilized to fill the inner chamber, simultaneously raises the weight or compresses the spring of the constant force stored energy means thereby storing the energy utilized to fill the implantable artificial bladder. When the discharge control means is opened, the stored potential energy of the weight or of the spring acting on the rolling diaphragm minus the resistance of the rolling diaphragm produces a pressure on the storage area or the inner chamber 6. That force produces a pressure in the biological fluid sufficient to discharge the biological fluid from the inner chamber but less than the peristaltic pressure of the ureter. Consequently, the stored biological fluid flows out of the outlet conduit through the patient's own urethra or through an artifical urethra and to the outside of the patient, but no biological fluid passes from the inner chamber or the inlet conduit, back through the patient's ureter.

DESCRIPTION OF THE PREFERRED EMBODIMENTS

The following devices illustrate the invention and its use. The devices are not intended to limit the claims in any manner whatsoever.

An apparatus as shown in FIG. 1 was made as follows:

A rigid outer shell was constructed of PVC pipe with plastic end caps. A hole was made in the top of the pipe to serve as an exterior vent. The rolling diaphragm (Bellofram 4-450-275-FCJ) was enclosed in the rigid outer shell. The inlet conduit comprised a 5 mm diameter, 30 cm long rubber hose which emptied through an inlet orifice of similar diameter into an inner chamber.

The outlet conduit comprised a 5 mm diameter rubber tube 25 cm in length. A discharge control means was placed in the outlet conduit. A weight of 1.2 pounds was placed on the top of the rolling diaphram comprising the constant force stored energy means. The bladder was characterized by measuring bladder pressure as a function of stored fluid volume. The bladder was initially filled using a large pressure head reservoir of about 30 cm of water, and bladder pressure was measured using a steady water column. The internal bladder pressure was determined by subtracting the height of the water level in the bladder form the height of the water level in the column. A fixed volume of water was then removed from the bladder and the pressure was remeasured. Fill volume and discharge rates were measured separately by methods known to those of ordinary skill in this art. Table 1 illustrates the major operating parameters of this embodiment. The fill volume at 15 cm water hydrostatic head obtained with a 1.2 pound weight comprising the constant force stored energy means was 440 ml. The back pressure to the ureter was 4.4 cm water and the discharge rate was 260 ml/min. FIG. 4 graphically illustrates implantable artifical bladder pressure (cm. water) versus volume (cc.) of this Embodiment 1.

Embodiment 2

The apparatus was made as described except that a 1.5 pound weight was substituted for the 1.2 pound weight of the constant force stored energy means. Table 1 illustrates the major operating parameters of this Embodiment 2. A fill volume at 15 cm water hydrostatic head of 450 ml was obtained. The back pressure was 4.7 cm water, and the discharge rate was 255 ml/min. FIG. 4 illustrates graphically the implantable artificial bladder pressure (cm. water) versus volume (cc.)

The above-mentioned patents and test methods are incorporated herein by references. All such obvious modifications are within the full intended scope of the appended claims. Many variations of this invention will suggest themselves to those skilled in the art in light of the above, detailed description. For example, the weight on the rolling diaphragm can be replaced with a spring operating against the chamber wall to bias the diaphragm, or a combination of a spring or springs and a weight can be used.

TABLE 1

|  | STORAGE WEIGHT | FILL VOLUME (AT 15 CM PRESSURE) | BACK PRESSURE | DISCHARGE RATE |
|---|---|---|---|---|
| Embodiment 1 | 1.2 lbs | 440 ml | 4.4 cm | 260 ml/min |
| Embodiment 2 | 1.5 lbs | 450 ml | 4.7 cm | 255 ml/min |

We claim:
1. An implantable artificial bladder for the collection of, the storage of, or the discharge of biological fluids comprising:
   (i) a leak-proof rigid outer shell comprised of a biocompatible material or a material having a surface coating of a biocompatible material;
   (ii) a rolling diaphragm inside said outer shell and attached to the inner surface of said outer shell, dividing the interior space of said outer shell into a leak-proof inner chamber and an outer chamber, said rolling diaphragm being deformable between two positions during introduction and discharge of biological fluid, the first said position corresponding to the full storage volume of implantable artificial bladder and the second said position corresponding to the empty volume of said implantable artificial bladder;
   (iii) an external vent in communication with said outer chamber;
   (iv) a constant force stored energy means operating on said rolling diaphragm and biasing it against said inner chamber;
   (v) at least one inlet conduit in open communication with said inner chamber and adapted to connect to at least one ureter of a patient, or to an artificial ureter, or to a Y-shaped nozzle adapted to connect to both ureters of a patient;
   (vi) at least one outlet conduit in open communication with said inner chamber below said rolling diaphragm and adapted to connect to the urethra of a patient or to an artificial urethra; and
   (vii) means downstream of said inner chamber for controlling the rate of flow of biological fluid exiting said inner chamber.

2. An implantable artificial bladder as defined in claim 1 wherein said constant force stored energy means (iv) comprises:
   (a) a weight on said rolling diaphragm located within said outer chamber operating to gravitationally bias said rolling diaphragm into said inner chamber;
   (b) at least one spring operating against said rolling diaphragm and the interior of said outer chamber; or
   (c) a combination of a and b.

3. An implantable artificial bladder as defined in claim 1 wherein said shell (i) is comprised of a poly(vinyl chloride), a poly(etherimide), or a polymer of acrylonitrile/butadiene/styrene, optionally coated with a biocompatible material.

4. An implantable artificial bladder as defined in claim 3 wherein said biocompatible coating material comprises silicone.

5. An implantable artificial bladder as defined in claim 1 wherein said rolling diaphragm (ii) comprises a silicon elastomer, a collagen, a polyactide, a polysuccinate, a polyoxalate, a fluorosilicone or an unsupported silicone.

6. An implantable artificial bladder as defined in claim 1 wherein the maximum fill pressure of said leak-proof inner chamber with said constant force stored energy means operating against said rolling diaphragm corresponds to a hydrostatic head of about 15 cm water.

7. An implantable artificial bladder as defined in claim 6 wherein the maximum static storing pressure of said leak-proof inner chamber with said constant force stored energy means operating against said rolling diaphram corresponds to a hydrostatic head of about 8 cm water.

8. An implantable artificial bladder as defined in claim 1 wherein the maximum storage volume of said inner chamber is about 500 ml.

9. An implantable artificial bladder as defined in claim 1 wherein said means for controlling the rate of flow (vii) comprises an internal balloon valve controlled by an external pump and a discharge valve assembly.

10. A method for the collection of, the storage of or the discharge of biological fluid said method comprising the steps of:
(a) providing an implantable artificial bladder comprising:
  (i) a leak-proof rigid outer shell comprised of a biocompatible material or a material having a surface coating of a biocompatible material;
  (ii) a rolling diaphragm inside said outer shell and attached to the inner surface of said outer shell, dividing the interior space of said outer shell into a leak-proof inner chamber and an outer chamber, said rolling diaphragm being deformable between two positions during introduction and discharge of biological fluid, the first said position corresponding to the full storage volume of said implantable artificial bladder and the second said position corresponding to the empty volume of said implantable artificial bladder;
  (iii) an external vent in open communication with said outer chamber;
  (iv) a constant force stored energy means operating on said rolling diaphragm and biasing it against said inner chamber;
  (v) at least one inlet conduit in open communication with said inner chamber and adapted to connect to at least one ureter of a patient, or to an artificial ureter, or to a Y-shaped nozzle adapted to connect to both ureters of a patient;
  (vi) at least one outlet conduit in open communication with said inner chamber below said rolling diaphragm and adapted to connect to the urethra of a patient or to an artificial urethra; and
  (vii) means downstream of said inner chamber for controlling the rate of flow of biological fluid exiting said inner chamber;
(b) attaching an inlet conduit of said implantable artificial bladder to the patient's ureter, to an artificial ureter attached to at least a portion of the patient's ureter, or to a Y-shaped nozzle and attaching a ureter to each of the remaining openings of said Y-shaped nozzle;
(c) attaching an outlet conduit of said implantable artificial bladder to the patient's urethra or to an artificial urethra;
(d) filling said implantable artificial bladder with said biological fluid by the natural peristaltic pressure of said ureter;
(e) storing said biological fluid by closing said means for controlling the rate of flow while storing a portion of said peristaltic pressure as potential energy in said constant force stored energy means; and
(f) discharging said biological fluid from within said implantable artificial bladder through said outlet conduit, and through the patient's urethra or through an artifical urethra by releasing at least a portion of said potential energy stored in said constant force stored energy means by opening said means for controlling the rate of flow.

11. The method as defined in claim 10 wherein said constant force stored energy means comprises:
(a) a weight on said rolling diaphragm located within said outer chamber operating to gravitationally bias said rolling diaphragm into said inner chamber;
(b) at least one spring operating against said rolling diaphragm and the interior of said outer chamber; or
(c) a combination of a and b.

12. The method as defined in claim 10 wherein said shell (i) is comprised of a poly(vinyl chloride), a poly(etherimide) or a polymer of acrylonitrile/butadiene/styrene, optionally coated with a biocompatible material.

13. The method as defined in claim 12 wherein said biocompatible coating material comprises silicone.

14. The method as defined in claim 10 wherein said rolling diaphragm (a)(ii) comprises a silicone elastomer, a collagen, a polyactide, a polysuccinate, a polyoxalate, a fluorosilicone, or an unsupported silicone.

15. The method as defined in claim 10 wherein the maximum fill pressure of said leak-proof inner chamber with said constant force stored energy means operating against said rolling diaphragm corresponds to a hydrostatic head of about 15 cm water.

16. The method as defined in claim 15 wherein the maximum static storing pressure of said leak-proof inner chamber due to said rolling diaphragm and said constant force stored energy means operating against said rolling diaphragm corresponds to a hydrostatic head of about 8 cm water.

17. The method as defined in claim 10 wherein the maximum storage volume of said inner chamber is about 500 ml.

18. The method as defined in claim 10 wherein said bladder filled with said biological fluid is adapted to discharge in about one minute or less.

19. The method as defined in claim 10 wherein said means for controlling the rate of flow (a)(vii) comprises an internal balloon valve controlled by an external pump and a discharge valve assembly.

* * * * *